(12) United States Patent
Qu

(10) Patent No.: US 9,842,240 B2
(45) Date of Patent: Dec. 12, 2017

(54) APPARATUS AND METHOD FOR DATA-TAG BASED OBJECT-TO-OBJECT APPLICATIONS

(71) Applicant: Lidong Qu, Beijing (CN)

(72) Inventor: Lidong Qu, Beijing (CN)

(73) Assignee: Lidong Qu, Beijing (CN)

( * ) Notice: Subject to any disclaimer, the term of this patent is extended or adjusted under 35 U.S.C. 154(b) by 0 days.

(21) Appl. No.: 15/383,190

(22) Filed: Dec. 19, 2016

(65) Prior Publication Data

US 2017/0103243 A1 Apr. 13, 2017

Related U.S. Application Data

(63) Continuation-in-part of application No. 14/461,408, filed on Aug. 17, 2014, now Pat. No. 9,560,146, which is a continuation-in-part of application No. 14/374,997, filed as application No. PCT/CN2014/082553 on Jul. 18, 2014, now Pat. No. 9,595,060.

(30) Foreign Application Priority Data

Sep. 18, 2013 (CN) .......................... 2013 1 0430210

(51) Int. Cl.
*H04N 7/16* (2011.01)
*G06K 7/14* (2006.01)
(Continued)

(52) U.S. Cl.
CPC ....... *G06K 7/1413* (2013.01); *G06K 7/10297* (2013.01); *G06K 7/10366* (2013.01); *G06K 7/1417* (2013.01); *G06Q 10/06* (2013.01); *G06Q 30/0207* (2013.01); *G06Q 30/0635* (2013.01); *G06Q 50/22* (2013.01); *H04L 67/16* (2013.01); *H04L 67/18* (2013.01); *H04N 21/2541* (2013.01); *H04N 21/2543* (2013.01); *H04N 21/25816* (2013.01); *H04N 21/6334* (2013.01); *H04N 21/237* (2013.01)

(58) Field of Classification Search
CPC .......... H04N 21/2543; H04N 21/4532; H04N 21/4542; H04N 7/163; H04N 7/165; H04N 7/17318; H04N 7/17309
USPC .... 725/4, 5, 25–28, 37–61, 91–93, 114–116; 709/217–232
See application file for complete search history.

(56) References Cited

U.S. PATENT DOCUMENTS 7,103,770 B2 * 9/2006 Conrath ................ H04L 63/083
709/231
7,246,158 B2 * 7/2007 Kitada ................ G06F 17/3089
707/E17.005

(Continued)

*Primary Examiner* — Annan Shang
(74) *Attorney, Agent, or Firm* — SV Patent Service

(57) ABSTRACT

The present invention relates to a method and system for data tagging in the field of computer technologies. In this method, a user terminal acquires tag data, obtains information about services and functions associated with the tag data, then interacts with target servers to exchange service and function information, and fulfills appropriate services and functions to complete the business application. The disclosed data tagging method and system allow user terminal to interact with directly target servers that are associated with relevant services and functions, which allows functions to be realized in distributed target servers, which simplifies the implementations of tag data, reducing the cost to setting servers. The disclosed data tagging methods allow more extensive applications of data tagging, improved user experiences, simplified processes, and lower costs.

19 Claims, 8 Drawing Sheets

(51) Int. Cl.
  *G06K 7/10*       (2006.01)
  *H04L 29/08*      (2006.01)
  *G06Q 10/06*      (2012.01)
  *G06Q 30/02*      (2012.01)
  *G06Q 50/22*      (2012.01)
  *H04N 21/254*     (2011.01)
  *H04N 21/2543*    (2011.01)
  *H04N 21/258*     (2011.01)
  *H04N 21/6334*    (2011.01)
  *G06Q 30/06*      (2012.01)
  *H04N 21/237*     (2011.01)

(56) References Cited

U.S. PATENT DOCUMENTS

| | | | | |
|---|---|---|---|---|
| 7,373,654 B1* | 5/2008 | Reid | ............ | H04L 63/20 |
| | | | | 713/155 |
| 7,607,022 B1* | 10/2009 | Qiu | ............ | H04N 7/1675 |
| | | | | 713/189 |
| 7,774,323 B2* | 8/2010 | Helfman | ............ | G06F 8/65 |
| | | | | 707/694 |
| 8,005,959 B2* | 8/2011 | Bernardi | ............ | G06F 21/575 |
| | | | | 709/213 |
| 8,094,661 B2* | 1/2012 | Salinger | ............ | H04L 12/2801 |
| | | | | 370/351 |
| 8,666,071 B2* | 3/2014 | Weber | ............ | H04N 21/2143 |
| | | | | 380/200 |
| 8,675,488 B1* | 3/2014 | Sidebottom | ............ | H04L 67/141 |
| | | | | 370/229 |
| 2002/0154892 A1 | 10/2002 | Hoshen | | |
| 2007/0101351 A1* | 5/2007 | Bagsby | ............ | G06Q 30/0613 |
| | | | | 725/1 |
| 2008/0048044 A1 | 2/2008 | Zhao | | |
| 2011/0299548 A1* | 12/2011 | Chen | ............ | G06Q 20/10 |
| | | | | 370/401 |
| 2013/0282592 A1* | 10/2013 | Zambrana | ............ | G06Q 30/012 |
| | | | | 705/302 |
| 2014/0222967 A1* | 8/2014 | Harrang | ............ | H04L 67/10 |
| | | | | 709/219 |
| 2016/0134912 A1* | 5/2016 | Dillon | ............ | G06F 21/10 |
| | | | | 725/25 |

* cited by examiner

APPARATUS AND METHOD FOR DATA-TAG BASED OBJECT-TO-OBJECT APPLICATIONS

BACKGROUND OF THE INVENTION

The present application relates to the field of computer application technologies, especially the field of data coding and data tagging.

Two-dimensional (2D) codes (also referred as two-dimensional barcodes, data matrix codes or QR codes) have large information capacity, high security, high rate of data retrieval, and error correction ability. After they were invented, 2D codes have been widely applied to logistics and operations management, and identification card management.

With increased popularity of smart phones, 2D codes can be captured and uploaded onto real-time Internet by smart phones in real time and used cross-media channels, which enable them to find wide applications in Object-to-Object (OTO) fields, such as information acquisition, mobile shopping, commodity counterfeiting, identity authentication, coupon distribution, and so on.

The mobile OTO applications of 2D codes currently focus on providing convenience in e-commerce, but they still lack in-depth applications.

On challenge to conventional 2D codes is that the servers that issue the 2D codes are responsible for the whole application process after the 2D codes are issued. For complex business applications, issuing 2D codes with comprehensive functions and integration of various stages of 2D code application require a lot of labor and financial investments, which poses a barrier to 2D codes' application in large and complete business models. There is therefore a need to simplify the processes, in order for 2D codes to be effectively used in a wider range of and especially large-scale business applications. Moreover, there is also a need for better user experiences in 2D code applications.

SUMMARY OF THE INVENTION

The present application discloses systems and methods intended to overcome the above mentioned disadvantages in the conventional systems. The disclosed data tagging methods and systems are simplified and easier to use comparing to conventional technologies, which are suitable for large scale applications. The disclosed data tagging methods and systems also provide better user experiences and low-cost data tagging methods and systems.

To achieve the above objectives, the disclosed data tagging methods can include one or more of the following steps:

(1) A user terminal acquires tag data, and parses the tag data to obtain a set of information about the services and functions related to a business application. The service information and function information correspond to respective target servers;

(2) The user terminal and the target servers exchange information about the services and functions in order to accomplish the services and functions, and fulfill the business application.

Step (1) in the disclosed method can include the following steps:

(a) The user terminal acquires tagging data from a data tag issuing server, parses the tag data, and obtains corresponding information about the business application in the tag data;

(b) Based on the information about the business application, the user terminal obtains the set of service and function information and information about target servers related to the services and the functions.

The service and function information can include service Software Development Kits (SDK) and function SDKs respectively corresponding to the services or functions. The service SDK and the function SDK respectively include information about their respective target servers, comprising application programming interface (API), parameters, and protocol associated with the target servers.

Step (2) in the disclosed method can include one or more of the following steps:

(a) based user operations, the user terminal selects some or all in the set of service and function information;

(b) The user terminal interacts with each target server to exchange the selected service and function information, to accomplish appropriate services and functions, and to complete the business application.

In the disclosed method, the step of user terminal interacting with each target server to exchange the selected service and function information includes the following steps:

The user terminal determines whether the selected service and function information will be exchanged with the target servers in sequential or in parallel order;

The user terminal exchanges the selected service and function information with the target servers in sequence or in sequential or in parallel order.

The present disclosure also provides a data tagging system comprising a user terminal, which can include a tag data acquisition module, a tag data analysis module, and an interaction control module. The tag data acquisition module is configured to acquire data from data tags and store the data. The tag data analysis module parses the tag data to obtain a set of data corresponding to services and functions for business applications. The interaction control module exchanges service and function information with corresponding target servers, to accomplish appropriate services and/or functions, and to complete the business application.

The disclosed data tagging system also includes a data tag issuing server that is configured to provide, to the user terminal, tag data according to the services as well as service and function information, corresponding to respective target servers.

In the disclosed data tagging system, the data tag issuing server can store a list of application services and corresponding service and function information, and information about target servers associated with the service and function information. The target server information includes API, parameters, and protocol about the associated target server.

In the disclosed data tagging system, the user terminal can be a wired or a wireless terminal, wherein the data tag issuing server is connected to the user terminal through a computer network.

In the disclosed data tagging system, the user terminal further includes a selection control module operated by a user and configured to select some or all in the set of the service and function information.

In the disclosed data tagging system, the user terminal further includes a sequence control module configured to determine the order (i.e. sequential parallel) of the selected service and function information to exchange with target servers.

In the disclosed data tagging method and system, the tag data acquisition module in the user terminal obtains tag data; the tag data analysis module parses the tag data to obtain a set of data corresponding to services and functions for business applications; the interaction control module exchanges service and function information with corresponding target servers, to accomplish appropriate services and/or functions, and to complete the business application. The disclosed data tagging method and system enables the user terminal to directly interact with target servers to accomplish the business application defined by the service and function information, which allows the tasks in complex business applications to be accomplished by distributed servers, and eliminates the need for building application servers in a network system. The disclosed data tagging method and system can thus reduce the cost for application service providers to building dedicated application servers, allow the data tags to be used more broadly, and provide better user experiences and low-cost data tagging methods and system.

These and other aspects, their implementations and other features are described in detail in the drawings, the description and the claims.

DETAILED DESCRIPTION OF THE INVENTION

The disclosed invention can be more clearly understood with the following detailed descriptions of the exemplified embodiments.

Figure 1:
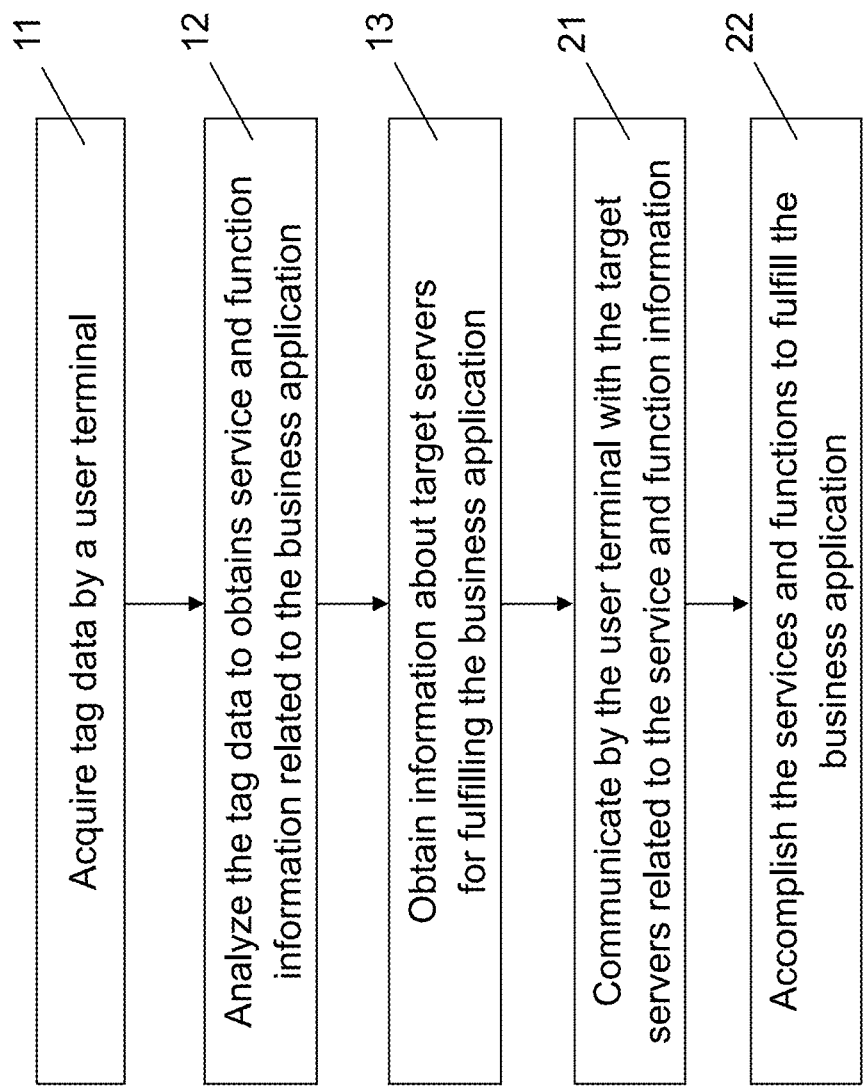
FIG. 1 is a data tagging flow diagram in accordance with some embodiments of the present invention.

A data tagging flow diagram in accordance with disclosed method is shown in FIG. 1.

In some embodiments, referring to FIG. 1, the disclosed data tagging method can include the following steps:

Step 1: the user terminal acquires data from data tag (step 11) which can be one-dimensional barcode, two-dimensional or three-dimensional code. The data tag can also include a RFID tag, and near field communication (NFC) data. The user terminal analyzes the data tag to obtain a set of service and function information related to a business application (step 12). The service and function information are corresponding to respective target servers (step 13). Examples of target servers include data tag issuing server configured to generate data tags that define services, functions, and target servers that implement the services and the functions, analysis server configured to extract service and function information from tag data, selection servers configured to allow user to select a service, location server configured to determine a user's location, authentication server configured to authenticate user's identification, and purchase server configured to process a user's order.

Step 2: the user terminal exchanges the service and function information with the target servers (step 21) in order to accomplish the services and functions, and fulfill the business application (step 22).

Step 1 in the disclosed method can include the following detailed steps:

(a) The user terminal acquires tagging data from a data tag issuing server, parses the tag data, and obtains corresponding business application information in the tag data;

(b) Based on the business application information, the user terminal obtains a set of service and functions information, and information about target servers related to the services and functions. Service information and function information can include product information, location information, logistics, shopping mode selection, and order and payment information.

In some embodiments, the service and function information can include service Software Development Kits (SDK) and function SDKs corresponding to the services or functions. The service SDK and the function SDK respectively include information about their respective target servers, comprising application programming interface (API), parameters, and protocol associated with the target servers.

Step 2 can include one or more of the following detailed steps:

(a) Based user operations, the user terminal selects some or all in the set of the service and function information;

(b) The user terminal interacts with each target server to exchange the selected service and function information, to accomplish appropriate services and functions, and to complete the business application.

In some embodiments, the step of user terminal interacting with each target server to exchange the selected service and function information includes the following steps:

The user terminal determines whether the selected service and function information will be exchanged with the target servers in sequential or in parallel order;

The user terminal exchanges the selected service and function information with the target servers in sequence or in sequential or in parallel order.

Figure 2:
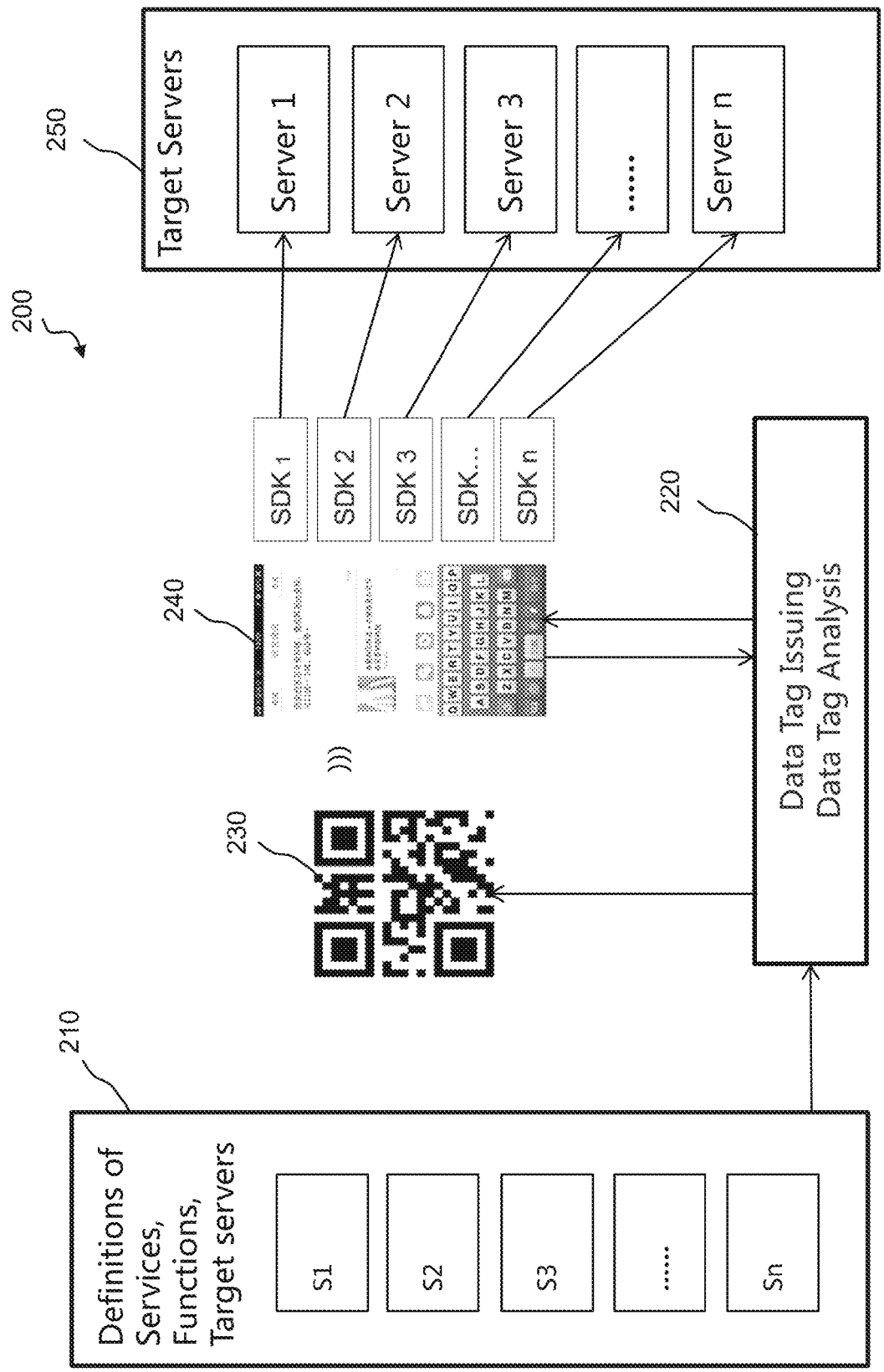
FIG. 2 is a schematic diagram of a computer network system for providing services using data tags in accordance with some embodiments of the present invention.

As shown in the above examples and illustrated in FIG. 2, a computer network system 200 for providing services using data tags includes a service definition server 210, one or more data-tag servers 220 for generating and issuing data tag (e.g. 2D code) and for analyzing data obtained from data tags, data tags 230 published on electronic media or printed on paper media, a smart user terminal 240 (e.g. a smart phone) installed with a software application configured to capture an image of the data tag and decode the data tag, which is subsequently analyzed by the data-tag server 220, and one or more target servers 250 that provide services for business applications.

The user terminal 240 can include a smart phone or a tablet computer equipped with a camera, handheld scanner, and RFID sensing device. The user terminal 240 can include a tag data acquisition module, a tag data analysis module, and an interaction control module. The tag data acquisition module is configured to acquire data from data tags and store the data. The tag data analysis module parses the tag data to obtain a set of data corresponding to services and functions for a business application. The interaction control module exchanges service and function information with corresponding target servers 250, to accomplish appropriate services and/or functions, and to complete the business application.

The data-tag server 220 is configured to provide, to the user terminal 240, tag data according to the services as well as service and function information, corresponding to respective target servers 250. In some embodiments, at least part of data tag decoding tasks is conducted by the data-tag server 220. The user terminal 240 can be a wired or a wireless terminal, wherein the data-tag server 220 communicates with the user terminal 240 through a computer network.

In the disclosed data tagging system, the data-tag server 220 that issues data tag can store a list of application services and corresponding service and function information, and information about target servers 250 associated with the service and function information. The target server information includes API, parameters, and protocol about the associated target servers 250.

Still referring to FIG. 2, service information and function information can include product information, location information, logistics information, shopping mode selection, and order and payment information. In some embodiments, the service and function information include SDK 1, SDK 2 . . . , SDK n, which can include service Software SDKs and function SDKs corresponding to the services or functions. The service SDK and the function SDK respectively specify information about their respective target servers 250, such as application programming interface (API), parameters, and protocol associated with the target servers 250.

In some embodiments, the user terminal 240 further includes a selection control module operated by a user and configured to select some or all in the set of the service and function information.

In some embodiments, the user terminal 240 further includes a sequence control module configured to determine the order (i.e. sequential parallel) of the selected service and function information to exchange with target servers.

By realizing OTO service definitions, integration, and collaboration, the disclosed system and methods transformed how services are organized and provided, can achieve real-time services by collaboration across organizations, and enable flexible combination of services, refinement of service units, and automated service coordination.

The above discussed data tagging methods and system are further illustrated by following examples:

Example 1: Product Ordering in Response to Tag Data

During store shopping, a consumer can use a mobile phone to take picture of data tag such as a 2D code on a commodity. An application (i.e. APP) installed on the mobile phone can decode the 2D code in the captured image and obtain application service embedded in the 2D code to order the commodity. The consumer can also obtain service information and function information such as product information, location information, logistics information, shopping mode selection, and order and payment information.

Specifically, the mobile phone first uses the application to connect to the server that maintains the product information via a mobile wireless network, acquires the product information, and displays it on the mobile phone. Then a location server (an example of a target server) determines the location of the consumer, and his or her relative location to the manufacturer and the storage warehouse. Web-based product order information is provided to the consumer. A purchase-method selection server (another example of a target server) integrates product and logistic information, and provides the consumer different purchase prices for different purchase methods. After the consumer confirms a purchase method, an order server (another example of a target server) transmits the order to the store for ordering from existing stock. Alternatively, the order server can send to order directly to the manufacturer and a logistics vendor through a computer network. Finally, the consumer can complete product purchase by making payment using his or her mobile phone. It should be noted that such 2D codes can also be printed directly in advertisements on newspapers and magazines. Consumers can process the product purchase by capture the image of the 2D codes on newspapers or magazines.

Thus, the generation of a 2D code for product ordering only requires that the service and function information and information about corresponding target servers to be contained in the corresponding SDKs. The user terminal can decode the 2D code and communicate with target servers directly to fulfill orders. Thus, the tasks of an order server are decomposed, which refines the 2D code application, providing more flexible services and functions, at lower cost.

Example 2: TV Set-Top Boxes

With the increased popularity of high-definition television, TV set-top boxes become common household electronic devices and in hotels. HD programs typically require users to pay a fee. However, the right to watch HD programs is tied to a specific TV set-top box. It is difficult for a user to watch the HD programs on a different TV set-top box. Moreover, another difficulty is to allow users to watch HD TV programs for a short term in hotels and other venues.

The data tagging method and system enable a data tag such as a 2D code to be displayed on TV after the TV set-top box is turned on. A user can take a picture of the 2D code using a mobile phone. The mobile phone can decode the 2D code, extract service information for the paid TV programs, and can obtain information about authentication, permissions, payment information, and other services and features.

First, the 2D code includes information about an authentication server (another example of a target server). The user can authenticate his or her identification through authentication server, and then register or login via an authorization server. If the user has purchased the pay-TV service, the authorization server sends to right-to-use confirmation, via a computer network, to the specific TV set-top box that the user is using, which allows the user to TV programs on the specific TV connected to the TV set-top box. Thus, the right to watch pay-TV is no longer tied to a specific TV set-top box. A consumer can watch pay-TV programs on any set-top box. If the user has not purchased a pay-TV service, the user can pay for the pay-TV service using the purchase information extracted from the 2D code on his or her mobile phone. The mobile phone can communicate directly with a purchase server (another example of a target server) to complete the order. The simplified pay-TV process is very suitable for short-term user of pay-TV services, in hotels etc.

Moreover, suitable data tags can include printed data codes (1D, 2D, 3D codes) and RFID tags. Examples of 2D codes include, but not limited to, two-dimensional barcodes, data matrix codes, or QR codes, etc. The 2D codes are first captured the smart user terminal and decoded by the software application on the smart user terminal to obtain tag data. The tag data is then parsed and analyzed by the analysis server to extract service and function information from the tag data. The software application (e.g. the mobile application on the smart phone) receives the service and function information and displays them on the smart terminal, as shown in FIG. 2. On the other hand, RFID tags can store service and function. Once retrieved, the mobile application can display such information at the user terminal without involving an analysis server.

The disclosed method and system include the following features:

1. Unified encoding rules for tag data. A data tag issuing server generates data tags according to services and functions to be provided and received, wherein the data tags can be retrieved by applications on intelligent user terminals.

2. Tag data retrieved by the intelligent terminals are defined by a combination of the data tag issuing server and intelligent user terminals, target servers that provide services, and collaborative approach to provide services.

3. An analysis server parses the tag data retrieved by the intelligent terminal to obtain SDKs related to target servers and services, and provides the SDKs the intelligent terminal.

4. The tag data is configured to provide and/or receive all services and functions necessary for a business application. A user can choose a service or function through a software application (e.g. a mobile App) at an intelligent terminal to interact with target servers, to accomplish actions and service contracts by coordinating services and the corresponding target servers.

The disclosed method and system can include one or more of the following advantages:

1. Flexible combination of services. Services can be flexibly combined and coordinated in response to data tag scanning by a user and user defined services. Tag data include SDKs that define relationship between different target servers based on services, target servers, and service contracts. The disclosed methods also assure coordination among services and in-depth specialization and optimization of resources.

2. More user friendly experiences. The disclosed tag data improve friendliness and user operability of the user interface. A user can select appropriate services at a user interface according to the specific combination of services that is desirable to the user.

3. In-depth utilization of a portfolio of services allows separation of authentication, payment, and service fulfillment, which increases the system security.

In the disclosed data tagging methods and system, a user terminal obtains data from data tag using a tag data acquisition module, parses the tag data using a tag data analysis module to acquire corresponding business applications and associated service and function information. An interaction control module in the user terminal then interactively communicates with target servers to exchange service and function information to fulfill business application. In the disclosed data tagging methods and system, the user terminal can implement business application based on the tag data, and directly accomplish services and functions by interacting with target servers that provide such services and functions, which eliminates the need for a central application server to fulfill the services. Different in complex business applications can therefore by accomplished by distributed interactive target servers, which effectively simplifies operation of utilizing tag data, reduces the costs of building application servers by service providers. The disclosed data tagging methods and system are more convenient and of lower cost, which allow wider applications data tagging, with improved user experiences.

Figure 3:
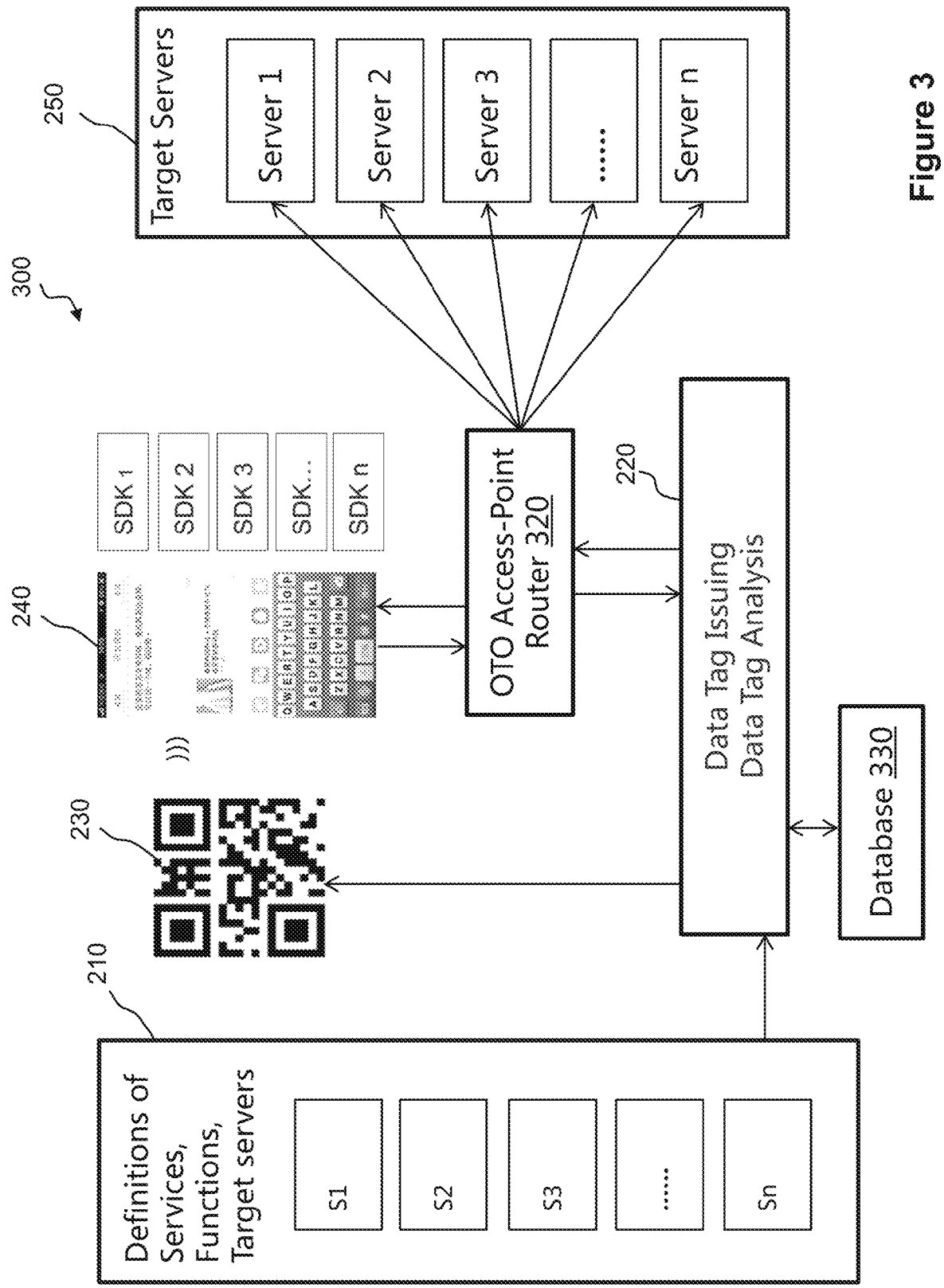
FIG. 3 is a schematic diagram of another computer network system for providing services using data tags in accordance with some embodiments of the present invention.

In some embodiments, referring to FIG. 3, a computer network system 300 for providing services using data tags includes a service definition server 210, one or more data-tag servers 220 for generating and issuing data tags (e.g. 2D code) and for analyzing data obtained from data tags, data tags 230 published on electronic media or printed on paper media, a data base 230 in connection with the one or more data tag servers 220, a smart user terminal 240 (e.g. a smart phone) installed with a software application configured to capture an image of the data tag and decode the data tag, which is subsequently analyzed by the data-tag server 220, and one or more target servers 250 that provide services for business applications.

The computer network system 300 also includes an OTO access-point router 320 that is configured to communicate with the user terminal 240, the data-tag server 220, and the one or more target servers 250. The OTO access-point router 320 can communicate with the user terminal 240 based on a wireless standard such as WiFi, WiMax, Bluethooth, IEEE 802.11, etc. At least part of the computer network system 300 (e.g. the data tag server 220 and the database 330) is provided by the OTO application service provider. The OTO access-point router 320 can be provided by the same OTO application service provider, or by a third party owner that partners with the OTO application service provider in providing data tag-based OTO application services.

The target servers 250 can include remote and local severs. Local servers can be distributed at locations close to user terminals, which increases data transfer and processing speeds for initiating and executing OTO application services. The target servers 250 can also include private and public servers. The private servers can function as master servers that drive the public servers (slave). For example, for most small companies, the user terminals 240 interact directly with public target servers 250 which perform most tasks for business applications. Large companies, on the other hand, can own most of the target servers in a private platform. The user terminals 240 only go to public target servers when needed. The private target servers perform most of the tasks.

Figure 4:
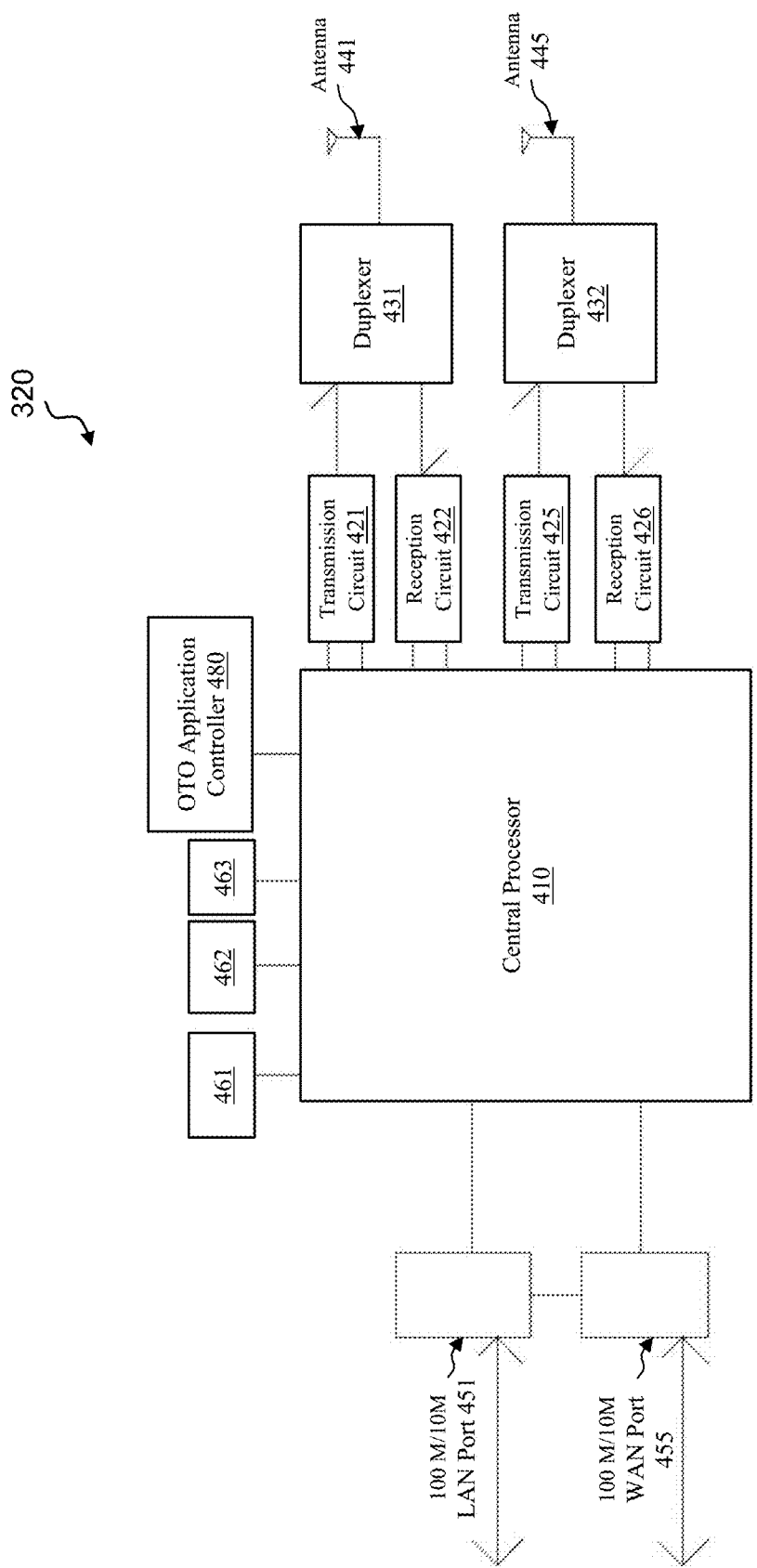
FIG. 4 shows a detailed system block diagram of an OTO access-point router in the computer network system in FIG. 3.

An exemplified detailed system block diagram of the OTO access-point router 320 is shown in FIG. 4. The OTO access-point router 320 performs the functions of a router but also includes the functions of a wireless access-point. The OTO access-point router 320 can include a central processor 410 that can perform processing tasks in a wireless router such as coding, decoding, and processing signals, and controlling other components in the OTO access-point router 320. The central processor 410 can output to and receive data from one or more transmission and reception circuits in for different wireless frequency bands (e.g. 2.4 GHz and 5 GHz). The central processor 410 can wirelessly communicate with the user terminal 240, the data-tag server 220, and the target servers 250 (FIG. 3). For example, in a first band, a transmission circuit 421 and a reception circuit 422 can be switched by a duplexer 431 to transmit or receive signals to or from an antenna 441. The transmission circuit 421 includes a power amplifier and a circuit for converting a data signal to an RF signal to be transmitted by the antenna 441. The reception circuit 422 includes a linear amplifier and a circuit for converting an RF signals received from the antenna 441 to a data signal. Portions of the transmission circuit 421 and the reception circuit 422 can be combined in a transceiver circuit. Similarly, in another band, a transmission circuit 425 and a reception circuit 426 can be switched by a duplexer 432 to transmit or receive signals to or from with an antenna 445. The wireless signals received by the antenna 441, 445 can include data tag information decoded from data tags. The central processor 410 can extract, from the data tag information, service and function information related to an application service as well as information about target servers to conduct tasks to fulfill the business application.

The central processor 410 can be connected to one or more wired communication ports such as a LAN (local area network) port 451 and a WAN (wide area network) port 455, to communicate with the data-tag server 220 and the target servers 250 (FIG. 3). The central processor 410 can also be connected with an oscillator 461, a memory 462, and a device description repository 463. The device description repository 463 stores a list of registered user terminals which are authorized to receiving OTO services. Once contacts are set up with these user terminals, the requests for service and function information and interactions with target servers can proceed without the need for authorization and log-in every time.

The OTO access-point router 320 also includes an OTO application controller 480 in communication with the central processor 410. The OTO application controller 480 stores information essential for fulfilling OTO services using data tags, which includes a product serial number (S/N) that uniquely identifies the OTO access-point router 320. The OTO application controller 480 can also store an OTO service activation ID. The product S/N and the OTO service activation ID are encrypted to avoid being tampered. The OTO application controller 480 can store terms for a leasing management (the time period and types of OTO services that are authorized on the router, etc.) consistent with the agreement stored in the database 330. The OTO application controller 480 can manage the transmission of content from the data tag server 220 and the target servers 250. The OTO application controller 480 can also take data inquiries from the user terminal 240 or from the data tag server 220 or the target servers 250 and conduct data analyses. In another example, the OTO application controller 480 can also manage advertisement, promotion, and product or service announcements sent from target servers to the user terminals. The OTO application controller 480 can also direct user terminals to private target servers 250 (as described above) if the user terminals are on the list of preapproved users.

In some embodiments, the OTO access-point router 320 can also perform some of the above described functions of the data-tag servers 220 (FIGS. 2 and 3). After a data tag is acquired and decoded by the user terminal 240, the decoded information is sent to the OTO access-point router 320. The OTO application controller 480 can extract service and function information related to an application service from the decoded data-tag information. The OTO application controller 480 can also extract information about a group of target servers that are set up to fulfill the application service. In this distributed approach, the OTO access-point router 320 is regularly (e.g. hourly, daily, etc.) updated by the one or more data-tag servers 220 about available application services, service and function information related to each application service, and information about target servers for fulfilling the application services. Such information are encrypted and securely stored in the OTO application controller 480.

Referring to FIGS. 3 and 4, the OTO access-point router 320 can include a physical data tag attached to its outer surface, or a data tag displayed in an electronic display panel. The soft electronic data tag displayed in a display panel on the OTO access-point router 320 is based on the data (product S/N, activation ID, etc.) stored in the OTO application controller 480. The data tag is encoded with the router's product serial number and the OTO service activation ID. The data tag can also be stored and encoded in an RFID (radio frequency identification) tag or NFC (near field communication) tag, which can be read by a respective RFID or NFC sensor in the user terminal 140. In some embodiments, the data in the electronic data tags can be controlled and varied by the OTO application controller 480.

This data tag can be originally issued by the one or more data servers 220 operated by the OTO service provider, and labeled on or stored in the OTO access-point router 320 during the router's manufacturing process. To set up the OTO access-point router 320 for OTO service, the person that installs the OTO access-point router 320 uses a user terminal 240 such as a smartphone to scan the data tag displayed on the OTO access-point router 320. The tag data analysis module in the user terminal 240 parses the tag data to obtain the product serial number and the OTO service activation ID. After proper authentication and log-in, the user terminal 240 can send the acquired information to the one or more data tag servers 220 operated by the OTO service provider, which activates the specific OTO access-point router 320 (based on its product S/N) to enable the fulfillment of OTO services based on data tags.

Once activated, the product S/N of the OTO access-point router 320 is tied to the router owner's user ID (UID), and stored in the database 330 operated by the OTO application service provider. The data tag server 220 assigns an association index, also stored in the database 330, which associates the router's product S/N and the owner's UID at the OTO service provider. The association index is subsequently sent to the user terminal 240.

The OTO application services of the OTO access-point router 320 are defined and governed by an OTO application agreement stored in the database 330. For example, the agreement can define the terms under which the OTO access-point router 320 is leased to a user.

Once set-up, the OTO access-point router 320 can facilitate fulfilling OTO services for user terminals 240. As described above, a user terminal 240 (which may be different from the user terminal used to activate the OTO access-point router) can be a smart phone or a tablet computer equipped with a camera, handheld scanner, and RFID sensing device. The user terminal 240 can include a tag data acquisition module, a tag data analysis module, and an interaction control module. The tag data acquisition module is configured to acquire data from data tags and store the data. The tag data analysis module parses the tag data to obtain a set of data corresponding to services and functions for a business application. The interaction control module exchanges service and function information with corresponding target servers 250, to accomplish appropriate services and/or functions, and to complete the business application. The one or more data-tag servers 220 can provide tag data according to the services as well as service and function information, corresponding to respective target servers 250. In some embodiments, at least part of data tag decoding tasks is conducted by the data-tag server 220.

The user terminal 240 can be a wired or a wireless terminal that can communicate with the data-tag server 220 via the OTO access-point router 320 in a wired and wireless computer network. The database 330 can store a list of application services and corresponding service and function information, and information about target servers 250 associated with the service and function information. The target server information includes API, parameters, and protocol about the associated target servers 250. Using the information obtained from the data tag, the user terminal 240 can communicate with the target servers 250 via the OTO access-point router 320, to request the target servers 250 to fulfill various tasks specified in the service and function information in order to fulfill the business application.

The service information and function information can include product information, location information, logistics information, shopping mode selection, and order and payment information. In some embodiments, the service and function information include SDK 1, SDK 2 . . . , SDK n, which can include service Software SDKs and function SDKs corresponding to the services or functions. The service SDK and the function SDK respectively specify information about their respective target servers 250, such as application programming interface (API), parameters, and protocol associated with the target servers 250.

In some embodiments, the user terminal 240 further includes a selection control module operated by a user and configured to select some or all in the set of the service and function information. In some embodiments, the user terminal 240 further includes a sequence control module configured to determine the order (i.e. sequential parallel) of the selected service and function information to exchange with target servers.

By realizing OTO service definitions, integration, and collaboration, the disclosed system and methods transformed how services are organized and provided, can achieve real-time services by collaboration across organizations, and enable flexible combination of services, refinement of service units, and automated service coordination.

Figure 5:
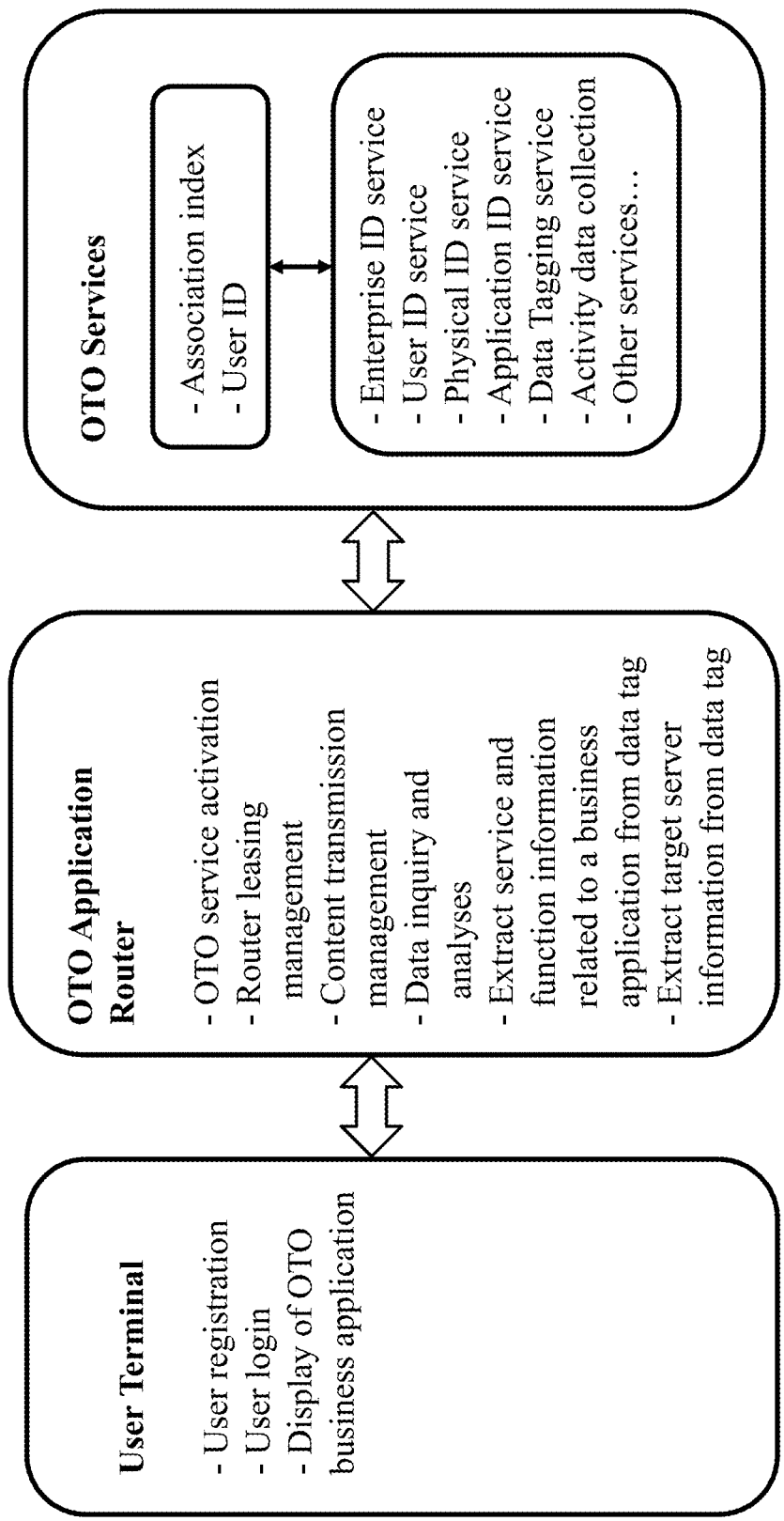
FIG. 5 illustrates exemplified functions of the OTO access-point router, the user terminal, the one or more data-tag servers, and the target servers in the computer network system in FIG. 3.

FIG. 5 illustrates some exemplified functions of the OTO access-point router 320, the user terminal 240, and OTO services that can be fulfilled by the computer network system 300 (FIGS. 3 and 4). The user terminal allows a user to register OTO service at an OTO service provider, and log into such a service. The user terminal 240 displays relevant OTO service information received from the data-tag server 220, the target servers 250, and the OTO access-point router 320.

As described above, the OTO access-point router 320 stores information needed to activate OTO service of the OTO access-point router 320 such as produce S/N and OTO activation ID. If applicable, the OTO access-point router 320 can also store information about equipment leasing.

The OTO access-point router 320 can manage the transmission of content from the data tag server 220 and the target servers 250. In Example 2 above, the OTO access-point router 320 can control the type and the rates of content (e.g. including customized news, movies, TV shows, and advertisements) being delivered to the TV set-top boxes and TV.

The OTO access-point router 320 can also take data inquiries from the user terminal 240 or from the data tag server 220 or the target servers 250 and conduct data analyses. In Example 1 above, the OTO access-point router 320 can record the types of products the user is interested, the times and frequencies of the product ordering, and the location of the user terminal 240. In Example 2 above, the OTO access-point router 320 can collect user's TV watching patterns. Relevant information can be reported to target servers 250 so their services can be improved.

In some embodiments, as described above, the OTO application controller 480 in the OTO access-point router 320 can store information about available application services, service and function information related to each application service, and information about target servers for fulfilling the application services. Such information is regularly (e.g. hourly, daily, etc.) updated by the one or more data-tag servers 220, which is encrypted and securely stored in the OTO application controller 480. When a data tag is acquired by a user terminal, the central processor 410 in the OTO access-point router 320 can extract service and function information related to an application service from the data tag, and information about target servers for fulfilling the application service, without having it performed at a remote data-tag server. The OTO access-point router 320 can send the service and function information related to an application service to the user terminal 240 via the transmission circuits 421 or 425 and their reception antenna 431, 432.

Still referring to FIG. 5, OTO services that can be fulfilled by the OTO access-point router 320, the one or more data-tag servers 220 and the target servers 250 include producing an association index, producing or linking to a user ID, issuing data tags, activity data collection, and providing services for enterprise IDs, physical IDs, and application IDs.

Figure 6:
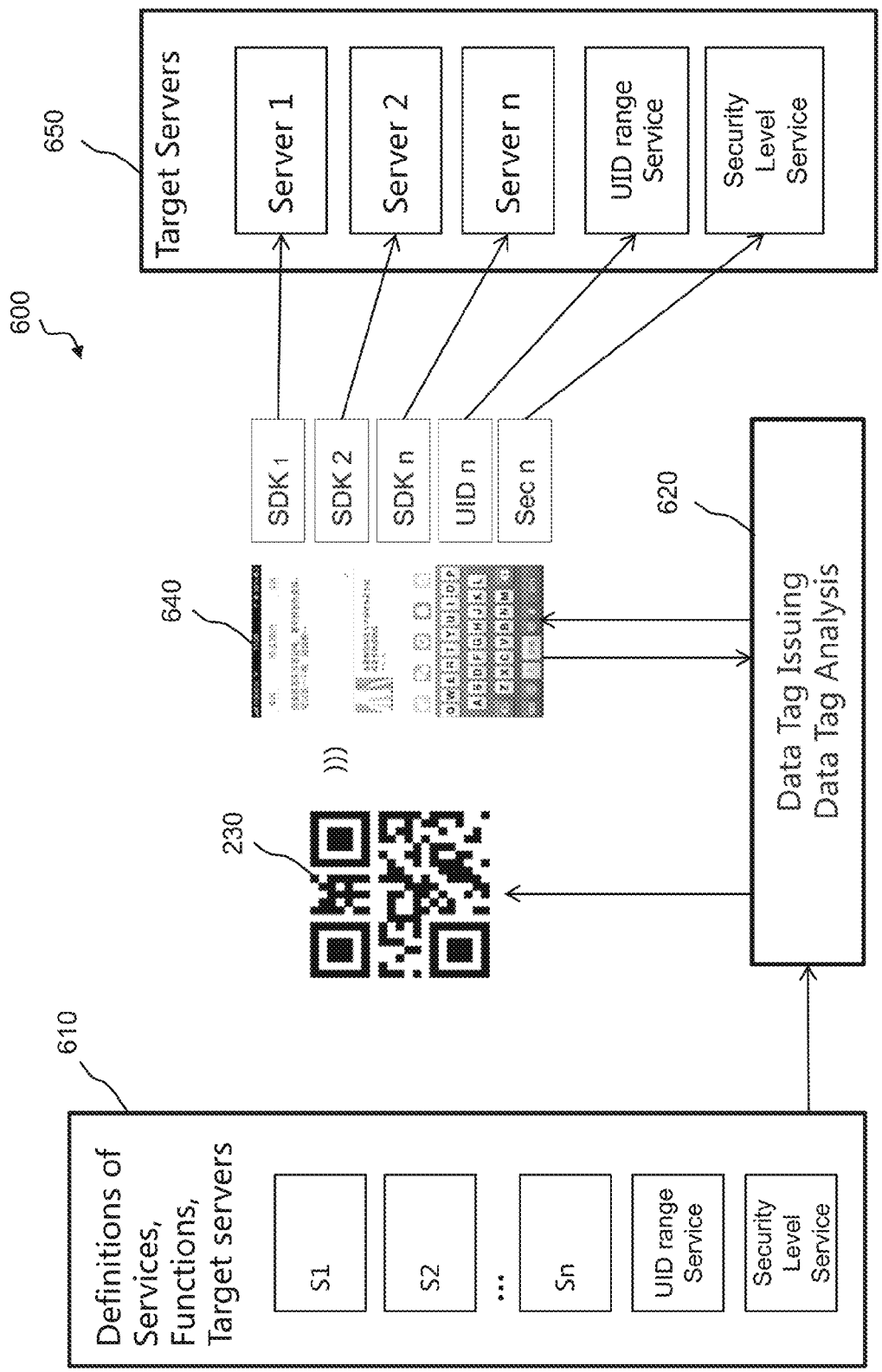
FIG. 6 is a schematic diagram of another computer network system for providing services using data tags in accordance with some embodiments of the present invention.

In some embodiments, referring to FIG. 6, a computer network system 600 for providing services using data tags includes a service definition server 610, one or more data-tag servers 620 for generating and issuing data tag (e.g. 2D code) and for analyzing data obtained from data tags, data tags 630 published on electronic media or printed on paper media, one or more user terminals 640 (e.g. a smart phone, a tablet computer, etc.) installed with a software application configured to capture an image of the data tag and decode the data tag, which is subsequently analyzed by the data-tag server 620, and one or more target servers 650 that provide services for business applications. As described below, the number of user terminals 640 required is dependent on the nature service and the request and definition of the early users.

The service definition server 610 stores definitions and functions for services S1, S2, . . . Sn and target servers such as server 1, server 2 . . . server n for fulling the services. Moreover, the service definition server 610 stores users having identifications UID and their roles involved in the fulfillment of the services S1, S2 . . . , Sn. Such roles can include one or more requesters for a service, one or more recipients of a service, an approver for a task (such as payment) related to a service, one or more fulfillers for a service, a manager of the workflow for a service, etc. Additionally, the service definition server 610 stores security or access level Sec for the users. For example, a recipient of a service has a lower security level than a fulfiller of the service. A requester of a service has a lower security level than an approver for a payment. Data tags created and shared related to each service specifies one or more users having security levels that allow them to extract information from the data tags.

The user terminal 640 can include a smart phone or a tablet computer equipped with a camera, handheld scanner, and RFID sensing device. The user terminal 640 can include a tag data acquisition module, a security module, a tag data analysis module, and an interaction control module. The tag data acquisition module first acquires data from a data tag and transmits the user identification UID of the associated user to the data-tag server 620 to get authorization to access in the data tag. If the data-tag server 620 determines that the security level Sec of the user terminal 640 is sufficient, the data-tag server 620 can send decryption information to the user terminal 640 to allow it to access the service information. The tag data analysis module parses the tag data to obtain a set of data corresponding to services and functions for a business application. The interaction control module exchanges service and function information with corresponding target servers 650, to accomplish appropriate services and/or functions, and to complete the business application.

In some embodiments, a user may be assigned to multiple roles such as an initiator of a service can also be an approver. In that situation, the security level of the user is assigned to the highest security level of the all the roles to which user is assigned.

The data-tag server 620 creates the tag data according to the services as well as service and function information, corresponding to respective target servers 650. In some embodiments, at least part of data tag decoding tasks is conducted by the data-tag server 620. The user terminal 640 can be a wired or a wireless terminal, wherein the data-tag server 620 communicates with the user terminal 640 through a computer network.

In the disclosed data tagging system, the data-tag server 620 stores a list of application services and corresponding service and function information, and information about target servers 650 associated with the service and function information. The target server information includes API, parameters, and protocol about the associated target servers 650.

Still referring to FIG. 6, service information and function information can further include product information, location information, logistics information, shopping mode selection, and order and payment information. In some embodiments, the service and function information include SDK 1, SDK 2 . . . , SDK n, which can include service Software SDKs and function SDKs corresponding to the services or functions. The service SDK and the function SDK respectively specify information about their respective target servers 650, such as application programming interface (API), parameters, and protocol associated with the target servers 650.

In some embodiments, the service information and function information can include user identifications UID, the users' roles in services, and security levels for requesting, approving, and fulfilling tasks associated with services.

In some embodiments, the user terminal 640 further includes a selection control module operated by a user and configured to select some or all in the set of the service and function information.

In some embodiments, the user terminal 640 further includes a sequence control module configured to determine the order (i.e. sequential parallel) of the selected service and function information to exchange with target servers.

The one or more target servers 650 include server 1, server 2 . . . , and server n. The one or more target servers 650 include also include servers for managing user identification and user roles associated with a service, managing users' security levels for accessing information, request, and approving, and fulfilling tasks in a service. Examples of target servers include data tag issuing server configured to generate data tags that define services, functions, and target servers that implement the services and the functions, analysis server configured to extract service and function information from tag data, selection servers configured to allow user to select a service, location server configured to determine a user's location, authentication server configured to authenticate user's identification, and purchase server configured to process a user's order. Each target server can perform a part of a service, a service or more than one service. In some instances, a service is fulfilled by a collaboration of multiple target servers.

By realizing OTO service definitions, integration, and collaboration, the disclosed system and methods transformed how services are organized and provided, can achieve real-time services by collaboration across organizations, and enable flexible combination of services, refinement of service units, and automated service coordination.

The coordination of tasks required in fulfilling a service can be organized in a hierarchical structure. A sequence of tasks can be stored as a service chain in association with the data-tag server. A service block can include one or more task chains. A service zone can include one or more service blocks. Each of the tasks is related to and can be fulfilled by a target server. The server chain, the service block, and the service zone can require increased higher security levels. In addition to UID, the persons in charge of the service chains, the service blocks, and the services zones can each be assigned with a unique identification code and roles to manage their respective service chains, service blocks, and services zones.

Figure 7:
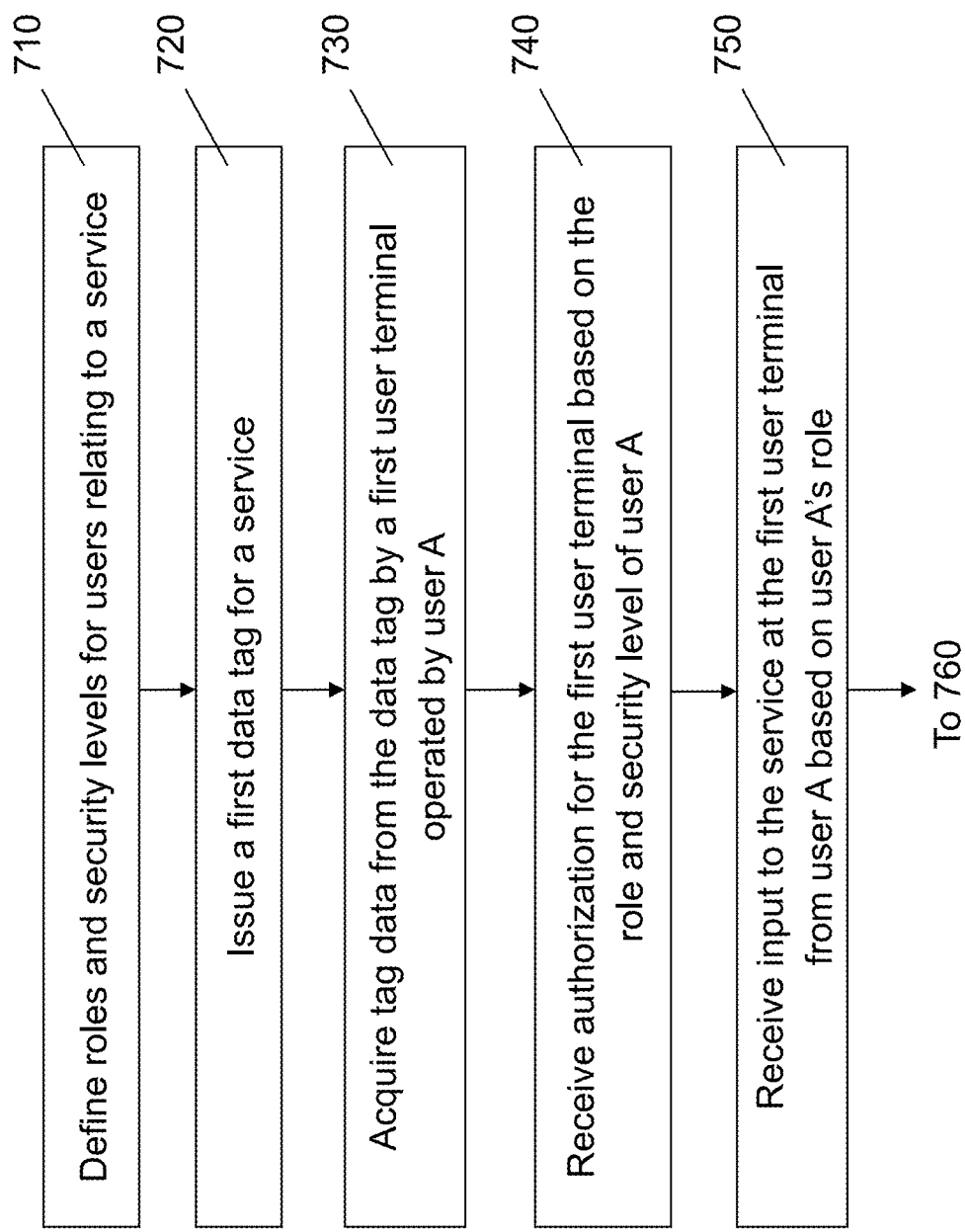
FIG. 7 is another data tagging flow diagram in accordance with some embodiments of the present invention.
Figure 7:
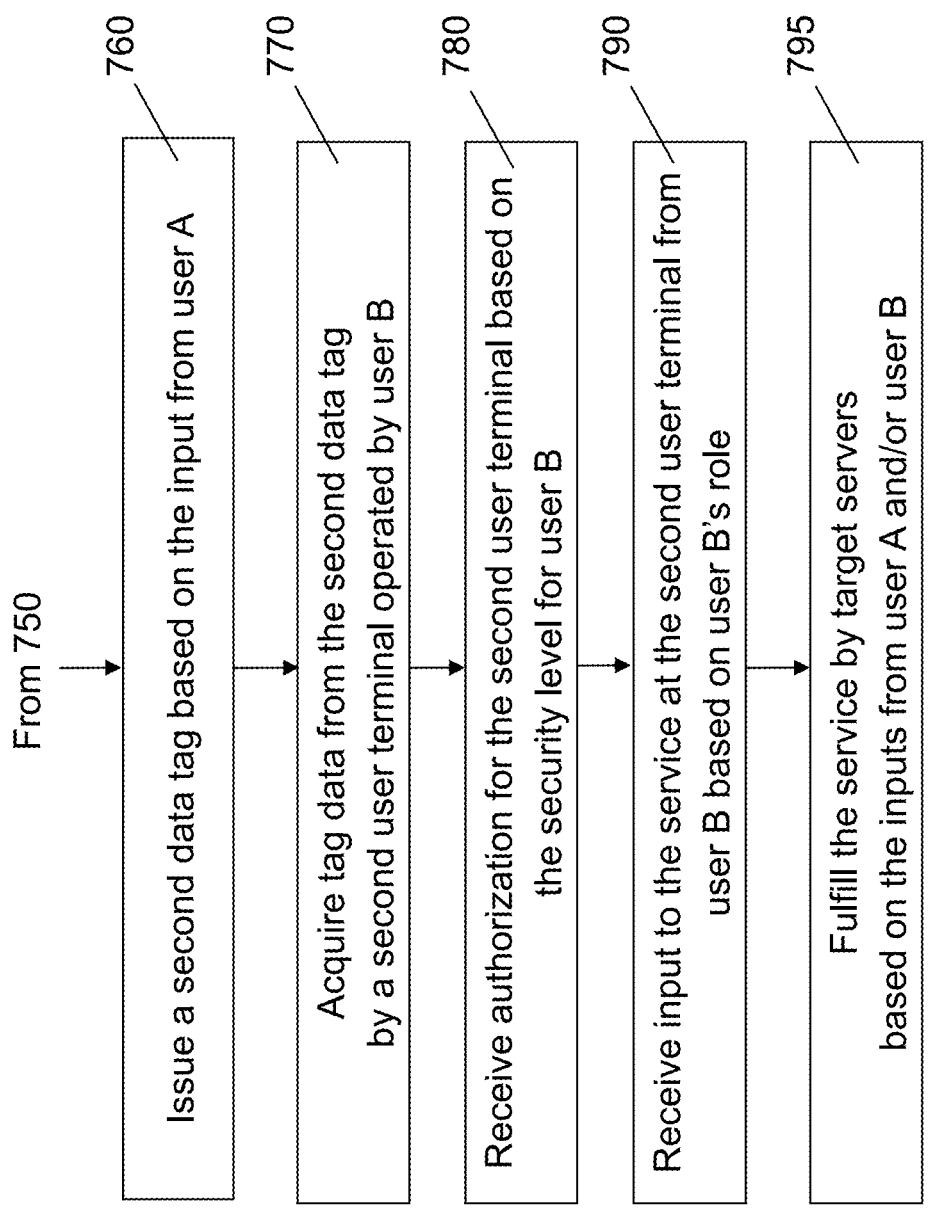

Referring to FIGS. 6 and 7, the presently disclosed data tagging methods can include one or more of the following steps: the roles and security levels of users are first defined (step 710). The users can include user A, user B, user C . . . , and so on. The role and security level of a user is defined (step 710) and stored in the service definition server 610. A first data tag is issued related to a service (step 720) by the data-tag server 620. The data tag can include one-dimensional barcode, two-dimensional or three-dimensional code. The first data tag can also include a RFID tag, and near field communication (NFC) data. The first data tag is sent to a first user terminal operated by user A. The first data tag can include service and function information, and information about target servers 650 associated with the service and function information. The target server information includes API, parameters, and protocol about the associated target servers 650. The first data tag can include or enable the first user terminal to communicate with data-tag server or target servers for the first user terminal to make selections in relation to the service.

The first user terminal acquires at least a portion of the tag data from the first data tag (step 730). The tag data prompts the first user terminal to contact the data-tag server 620 with the UID of user A and the specific service to which the first data tag is related. The data-tag server 620 can authorize (or decline) the first user terminal based on the role and security level of user A (step 740) in relation to the specific service involved. The authorization or decline is based on the security level associated with the UID of user A stored in the computer system.

Once approved, the first user terminal can analyze the data tag to obtain a set of service and function information related to a business application. The service and function information are corresponding to respective target servers. In some embodiments, at least a portion of the content in the data tag is encrypted and can be accessed only to users above certain security level. After the authorization of user A, the data-tag server 620 can send a passcode or decryption information to the first user terminal for it to decrypt a least a portion of the information extracted from the data tag. Service information and function information can include product information, location information, logistics, shopping mode selection, and order and payment information. In some embodiments, the service and function information can include service Software Development Kits (SDK) and function SDKs corresponding to the services or functions. The service SDK and the function SDK respectively include information about their respective target servers, comprising application programming interface (API), parameters, and protocol associated with the target servers.

The first user terminal provides user A's input based on user A's role (step 750) to the data-tag server 620 or the target servers 650. Such input can include user A's selection of service and function information such as product type and format, product count, delivery method, delivery time and destination, payment method, etc.

In some embodiments, the specification and fulfillment of a service can require the inputs and actions from multiple users who have different roles and security levels related to the service. In some cases, the need for additional users relating to a service is not known until the input from the first user (user A). In other words, the need for additional users is dependent on the input of the early (e.g. the first) users. The input to the service from the first user can include a request for another user to perform another task before the service can be fulfilled.

Optionally, if the input from user A demands, a second data tag is issued related to a service based on the input of user A (step 760) by the data-tag server 620. The second data tag is sent to a second user terminal operated by user B. The second user terminal acquires at least a portion of the tag data from the first data tag (step 770). Similar to user A and the first user terminal, the tag data in the second data tag prompts the second user terminal to contact the data-tag server 620 with the UID of user B and the specific service to which the second data tag is related. The data-tag server 620 can authorize (or decline) the first user terminal based on the role and security level of user B (step 780) in relation to the specific service involved. The authorization or decline is based on the security level associated with the UID of user B stored in the computer system.

Once approved, the first user terminal can analyze the data tag to obtain a set of service and function information related to a business application. The service and function information are corresponding to respective target servers. The second user terminal provides user B's input based on user B's role (step 790) to the data-tag server 620 or the target servers 650. Such input can include user B's selection of service and function information such as product type and format, product count, delivery method, delivery time and destination, payment method, etc. Finally, the service is fulfilled by the target servers 650 based on inputs from user A and optionally also the input from user B (step 795).

The above described data tagging methods can be further understood using the following examples.

Example 3: Defining and Tracking Multiple Roles with Multiple Data Tags in a Multi-Step Application The method of using multiple data tags in fulfilling a service involving multiple users can be applied to the purchase of a high value item. A staff member (or a child) uses a first data tag to search, selects, creates, or defines a product or service to be purchased. The staff member (or the child) then specifies another user (manager or parent) and prompts data-tag server to create a second data tag for the second user. The manager or parent (the second user) uses a second user terminal to extract information to review the product or service prepared by the staff member (or the child) and authorizes payment for the product and service. Based on the product or the service selected by the first user and the approval and the payment by the second user, the product or the service can be fulfilled by the target servers specified in the data tags. It should be noted that the above described steps can be performed, as mentioned above, by a single user who have been assigned to multiple roles and an appropriate highest security level among the multiple roles.

Example 4: A Platform and Processes for Medical Healthcare Services Using Distributed Data Tracking and Monitoring The above described system and method can be used to implement to manage complex data distributing, tracking, and monitoring in medical healthcare services. For example, the process of doctor visit and subsequent drug prescription involve multiple parties such as a patient, one or multiple doctors (family doctor, a specialist referred by the family doctor), one or more lab technicians for one or more tests and lab work, and a pharmacist. The healthcare coverage for such a visit can also involve a hospital or a clinic, an insurance company or a government healthcare program, a third party health care service provider, a pharmacy, home-based or wearable medical equipment and monitoring devices, the patient, etc.

Using the doctor visit, diagnostic and treatment as an example, the initial visit to a doctor or even an email or phone contact with a doctor can trigger the definition of a service, which defines the type of sickness, user ID, security level for the patient, his or her family member, the doctor, the insurance agency, etc. A doctor visit may trigger creation of a first data tag by the data-tag server in association with the first doctor visit or contact. Upon a request by the doctor seen in the first doctor visit, one or more data tags can be created by the data-tag server for lab works, for drug prescription, another visit to a referral doctor (such as a specialist), and for the payment to the initial doctor visit by the insurance company. These additional data tags must be scanned at the associated stages to verify user (patient) roles, user identity, and the security level of the user, as well as the type of task that the second user (e.g. pharmacy) to ensure accuracies of the tasks to be conducted.

Healthcare appointment can be initiated via home-based or wearable medical equipment and monitoring devices, when these equipment or devices have detected abnormal characteristics in a patient. The event of making such an appointment can trigger the creation of the first data tag, which can be scanned by the doctor's office at the time of the appointment. The data tag server can then be in contact with the doctor's office to receive information, requests, and follow-up tasks after the visit, which may lead to the issuance of a second data tag to track the follow-up activities.

The lab scans a data tag before a lab test is conducted to ensure accuracy and tracking. The completion of the lab works can further trigger creation of additional data tags by the data-tag server for a follow-up visit to the doctor. The additional data tag is scanned during the second doctor visit, which may trigger the creation of a visit to a specialist or a different doctor for a second opinion. Additional data tags can be created for drug prescription. As the pharmacy, the patient can scan such a data tag to confirm accuracy of the drug prepared for his or her visit, which also triggers authorization of payment by the insurance company for the drug prescription.

In the present specification, the present invention has been described with specific examples. However, it should be noted that various modifications and variations may be made without departing from the spirit and scope of the invention. Accordingly, the specification and drawings are to be regarded for illustrative rather than restrictive purposes.

What is claimed is:

1. A computer-implemented method for providing services using data tags, comprising:
    defining roles and security levels for users relating to a service, wherein the users include a first user;
    issuing a first data tag for a service by a data-tag server;
    acquiring tag data from the first data tag by a first user terminal operated by the first user;
    in response to acquisition of the tag data from the first data tag, receiving authorization for the first user terminal based on a role and a security level of the first user;
    receiving a first input to the service at the first user terminal from the first user based on the first user's role;
    fulfilling the service by one or more target servers based on the inputs by the first user;
    issuing a second data tag by the data-tag server based on the first input from the first user;
    acquiring tag data from the second data tag by a second user terminal operated by the second user, wherein the users include the second user;
    in response to acquisition of the tag data from the second data tag, receiving authorization for the second user terminal based on the security level for the second user;
    receiving a second input to the service at the second user terminal from the second user based on second user's role; and
    fulfilling the service by the one or more target servers based on the first input from the first user and the second input from the second user.

2. The computer-implemented method of claim 1, wherein the first user terminal is configured to receive a selection about the service from the first user, wherein the second user terminal is configured to receive an authorization for a payment for the service from a second user.

3. The computer-implemented method of claim 1, wherein the first data tag is issued in response to a first doctor visit by a patient.

4. The computer-implemented method of claim 3, wherein the second data tag is issued in relation to a lab test, a drug prescription, a referred doctor visit, a charge to an insurance company in response to the first doctor visit by the patient.

5. The computer-implemented method of claim 1, wherein the first input from the first user comprises a request for the second user to perform a task to enable the service to be fulfilled.

6. The computer-implemented method of claim 1, further comprising:
    receiving a selection from the first user terminal in relation to the service, wherein the service is fulfilled by the one or more target servers based on the selection of the first user.

7. The computer-implemented method of claim 1, wherein the roles include a requester, an approver, a recipient, or a fulfiller associated with the service.

8. The computer-implemented method of claim 1, wherein the first data tag includes service and function information related to the service, wherein the service and function information defines tasks required to fulfill the service as well as the one or more target servers to conduct the respective tasks, wherein the one or more target servers fulfill the service based on the service and function information.

9. The computer-implemented method of claim 1, wherein the service defines a chain of sequential tasks and a user assigned with a unique identification and a security level in charge of the chain of sequential tasks.

10. The computer-implemented method of claim 9, wherein the service defines a service block comprising one or more chain of sequential tasks and a user assigned with a unique identification and a security level in charge of the service block.

11. The computer-implemented method of claim 10, wherein the service defines a service zone comprising one or more service blocks and a user assigned with a unique identification and a security level in charge of the service zone.

12. The computer-implemented method of claim 1, wherein the first data tag comprises a one-dimensional code, a two-dimensional code, a two-dimensional barcode, a data matrix code, a QR code, or a three-dimensional code.

13. The computer-implemented method of claim 1, wherein the step of obtaining comprises decoding the first data tag to obtain information about the service.

14. The computer-implemented method of claim 13, wherein at least a portion of the decoding step is conducted by the data-tag server.

15. The computer-implemented method of claim 13, further comprising:
    sending decryption information from the data-tag server to the first terminal, wherein at least a portion of the decoding step is conducted using the decryption information.

16. A computer-implemented method for providing services using data tags, comprising:
    defining roles and security levels for users relating to a service, wherein the users include a first user;
    issuing a first data tag for a service by a data-tag server;
    acquiring tag data from the first data tag by a first user terminal operated by the first user;
    in response to acquisition of the tag data from the first data tag, receiving authorization for the first user terminal based on a role and a security level of the first user;
    receiving a first input to the service at the first user terminal from the first user based on the first user's role;
    fulfilling the service by one or more target servers based on the inputs by the first user, wherein the one or more target servers include at least one of a location server, a purchase-method selection server, or an order server, wherein the step of fulfilling the service comprises:
        determining a location of the first user terminal;
        allowing the first user terminal to select a purchase method by the purchase-method selection server;
        providing different pricing information from the purchase-method selection server to the first user terminal based on the selected purchase method; and
        processing an order submitted from the first user terminal by the order server, wherein the order is fulfilled based in part on the location of the first user terminal.

17. A computer-implemented method for providing services using data tags, comprising:
    defining roles and security levels for users relating to a service, wherein the users include a first user;
    issuing a first data tag for a service by a data-tag server;
    acquiring tag data from the first data tag by a first user terminal operated by the first user;
    in response to acquisition of the tag data from the first data tag, receiving authorization for the first user terminal based on a role and a security level of the first user;
    receiving a first input to the service at the first user terminal from the first user based on the first user's role;
    fulfilling the service by one or more target servers based on the inputs by the first user, wherein the one or more target servers comprise an authentication server, a permission server, or a payment server, the method further comprising:

enabling the first data tag to be displayed on a television device controlled by a TV set-top box;

authenticating an identification associated the TV set-top box by the authentication server; and based on the step of authentication, permitting a TV service to be provided to the TV set-top box by the permission server.

18. The computer-implemented method of claim 17, further comprising:

receiving a payment from the first user terminal by the payment server, wherein the TV service is permitted to be provided to the TV set-top box by the permission server after the payment is received.

19. The computer-implemented method of claim 17, wherein the first user terminal includes a mobile phone or a tablet computer.

* * * * *